United States Patent
Drevik (10) Patent No.: US 7,258,683 B2
(45) Date of Patent: Aug. 21, 2007

(54) ABSORBENT ARTICLE WITH DETACHABLY CONNECTED SIDE FLAPS HAVING INDENTATIONS AND OPENINGS

(75) Inventor: Solgun Drevik, Mölnylcke (SE)

(73) Assignee: SCA Hygiene Products AB, Gothenburg (SE)

( * ) Notice: Subject to any disclaimer, the term of this patent is extended or adjusted under 35 U.S.C. 154(b) by 378 days.

(21) Appl. No.: 10/322,431

(22) Filed: Dec. 19, 2002

(65) Prior Publication Data

US 2003/0139723 A1    Jul. 24, 2003

Related U.S. Application Data

(60) Provisional application No. 60/340,834, filed on Dec. 19, 2001.

(51) Int. Cl.
*A61F 13/15* (2006.01)
(52) U.S. Cl. .................. 604/385.04; 24/442
(58) Field of Classification Search .............. 604/383, 604/385.01–385.05, 386, 387, 389; D24/124–126
See application file for complete search history.

(56) References Cited

U.S. PATENT DOCUMENTS

| | | | |
|---|---|---|---|
| 4,389,211 A * | 6/1983 | Lenaghan .................... 604/383 |
| 4,655,759 A * | 4/1987 | Romans-Hess et al. 604/385.21 |
| 4,790,838 A * | 12/1988 | Pigneul et al. .............. 604/366 |
| 4,917,697 A * | 4/1990 | Osborn et al. .............. 604/387 |
| 5,108,385 A * | 4/1992 | Snyder ........................ 604/397 |
| 5,154,715 A * | 10/1992 | Van Iten ...................... 604/387 |
| 5,423,786 A * | 6/1995 | Fung et al. .................. 604/367 |
| 5,429,630 A * | 7/1995 | Beal et al. ............. 604/385.04 |
| 5,542,941 A * | 8/1996 | Morita ................... 604/385.04 |
| 6,251,097 B1 * | 6/2001 | Kline et al. ................. 604/387 |
| 2002/0058919 A1 * | 5/2002 | Hamilton et al. ....... 604/385.05 |
| 2002/0143315 A1 * | 10/2002 | Garrad et al. .......... 604/385.04 |

FOREIGN PATENT DOCUMENTS

| | | |
|---|---|---|
| EP | 0 359 501 A2 | 3/1990 |
| EP | 0 359 501 B1 | 12/1994 |
| EP | 0 527 171 B1 | 10/1996 |
| EP | 1 188 425 A2 | 3/2002 |
| SE | 514898 C2 | 5/2001 |
| WO | WO91/16873 A1 | 11/1991 |
| WO | WO97/15261 A1 | 5/1997 |
| WO | WO 01/15644 A1 | 3/2001 |

* cited by examiner

*Primary Examiner*—Tatyana Zalukaeva
*Assistant Examiner*—Laura C Hill
(74) *Attorney, Agent, or Firm*—Buchanan Ingersoll & Rooney PC (57) ABSTRACT

Absorbent article, such as a sanitary towel, a panty liner, an incontinence pad or the like, which article has two transverse end edges, two longitudinal side edges, a liquid-permeable surface layer, an essentially liquidtight backing layer, and an absorbent core located between the liquid-permeable surface layer and the essentially liquidtight backing layer and also side flaps at the longitudinal side edges on both sides of the absorbent core, the side flaps being folded and detachably tacked to the surface layer, said tacking being mechanical.

30 Claims, 10 Drawing Sheets

ABSORBENT ARTICLE WITH DETACHABLY CONNECTED SIDE FLAPS HAVING INDENTATIONS AND OPENINGS

This application claims priority under 35 U.S.C. § 119(e) to U.S. Provisional Application No. 60/340,834 entitled ABSORBERANDE ALSTER MED SIDOFLIKAR and filed on Dec. 19, 2001, the entire content of which is hereby incorporated by reference.

BACKGROUND

1. Technical Field

The present invention relates to an absorbent article, such as a sanitary towel, a panty liner, an incontinence pad or the like, which article has two transverse end edges, two longitudinal side edges, a liquid-permeable surface layer, a liquidtight backing layer, and an absorbent core located between the liquid-permeable surface layer and the liquidtight backing layer, and also side flaps at the longitudinal side edges on both sides of the absorbent core.

2. Background of the Invention

Some modern conventional sanitary towels and similar products have side flaps. The purpose of the side flaps is to attach the article to the briefs so that it does not lie askew by being folded around the edges of the briefs in the crotch portion and attached to the outside of the briefs. Another reason for providing a sanitary towel or the like with side flaps is that the risk of leakage occurring is reduced. Leakage often occurs in sanitary towels without side flaps as a result of the edges of the briefs in the crotch area becoming turned in over the upper side of the article. This usually happens when the sanitary towel is narrower than the width of the briefs in their crotch portion. Leakage can also occur when there is insufficient time for liquid to be absorbed in the central portion of the sanitary towel, and it runs out on the surface towards and over the side edges of the article where the liquid comes into contact with the underwear. An article with side flaps assists with positioning in the briefs and reduces the occurrence of leakage. An example of a document which describes the attachment of the sanitary towel is EP 0 359 501.

On supply to the consumer, sanitary towels and similar products are often folded for packing and packed. In this context, "folded for packing" means that the side flaps are folded over the product so that they come to lie against the liquid-permeable surface layer in the central part of the product when supplied, and that the product is folded one or more times in the transverse direction or longitudinal direction in order that its size is reduced so that the product is easier to handle. Generally, the products are supplied packed, for example multipacked or individually packed. A multipacked product is characterized by a number of products lying side by side, packed in a common outer packing. An individually packed product is characterized by each individual product first being packed in its own packing which is then packed together with further individually packed products to form a larger unit in a common outer packing. Suitable materials for individual packing of the product can include, for example, an essentially liquidtight plastic film, a tissue layer or a similar thin flexible material. The common outer packing can include, for example, cardboard or plastic.

A product folded for packing is considerably smaller and significantly easier for the consumer to store and carry in a bag, trouser pocket or the like. If the products are moreover individually packed, the possibility of keeping the products hygienically is improved, so that they do not become soiled by dirt and dust when they are stored in, for example, a bag, pocket or the like.

Products with side flaps have generally been difficult to fold and pack in controlled ways during manufacture compared with products without side flaps. At a slow production rate, the side flaps of the products can be folded in a controlled manner but, at an increased production rate, this becomes difficult. The reason why the side flaps are incorrectly folded may be, for example, that the folding unit in the production machine does not function mechanically at a high rate. Another reason for the side flaps being incorrectly folded may be that the materials from which the products are made and of which the surfaces come to lie against one another when the side flaps are folded over the article have too low friction against one another. Low friction between the materials means that they do not cling to one another but slide apart.

However, the comfort to the wearer can be improved if material surfaces which will lie against the skin of the consumer have low friction. Low friction of a material means a nice, soft surface. As it is considerably more important to supply products which feel comfortable to the consumer, it is important for the problem of folding products for packing to be solved without it being necessary to forgo the quality of the material.

An incorrectly folded side flap, which projects from the product in some way, increases the likelihood of machine stoppage occurring because projecting side flaps catch on machine parts on the way through the production machine, which can lead to production being disrupted.

Another problem which can arise when the side flaps of the product are incorrectly folded is that packing the article in an individual packing is made difficult. For example, when the packing material is sealed outside the edges of the product folded for packing so as to form an individual packing, incorrectly folded side flaps can accidentally end up in the seal. A product with its side flaps caught in the seals of the individual packing is unfortunately not always detected during product control but is discovered only when the consumer is about to use the product. A product with its side flaps caught in the seals of the individual packing will be pulled apart on opening and has to be discarded by the consumer. A product with incorrectly folded side flaps moreover creates a slipshod impression which may give the consumer the impression that the functioning of the product would be worse than is actually the case.

Another problem which can arise when the side flaps are incorrectly folded is an increased risk of the protective layer on the means of attachment of the side flaps being creased or turned up from the adhesive surfaces so that the adhesive surfaces become exposed and attach themselves to surfaces other than the adhesive protective layers. Products with the adhesive surfaces of their side flaps attached to surfaces other than the protective layers may be spent and not useable by the consumer.

A further problem can arise in instances when relatively rigid material is used for the side flaps of the product. Incorrect folding of the side flaps may then become lasting, which makes it difficult to fold the side flaps around the edges of the briefs in the crotch area.

One way of reducing the problem of side flaps being incorrectly folded during production is described in, for example, EP 0 527 171. In an illustrative embodiment in EP 0 527 171, the side flaps are folded down over the liquid-permeable surface layer of the article and are held in place by a skin-friendly adhesive. One disadvantage of the illustrative embodiment described in EP 0 527 171 is the increased cost for the adhesive which is to hold the side flaps in place. Another disadvantage is that it is extremely difficult to control the strength of the adhesive so that the side flap lies sufficiently firmly against the liquid-permeable surface layer of the product. If the side flap is attached too loosely to the liquid-permeable surface layer, it will come loose during manufacture and packing. In instances when the side flap lies excessively firmly against the liquid-permeable surface layer of the product, there is a great risk that the liquid-permeable surface layer of the product and/or the side flap will be torn apart when the side flap is lifted up from the liquid-permeable surface layer. Another disadvantage is that the adhesive impairs the capacity of the product for admitting liquid into the product.

A further disadvantage of using adhesive as the means of attachment of the side flaps to the liquid-permeable surface layer of the product is that the adhesive areas which remain on the liquid-permeable surface layer after the side flaps have been lifted up from the liquid-permeable surface layer can feel uncomfortable to the consumer as the adhesive area does not have the same surface characteristics as the rest of the upper side.

OBJECTS AND SUMMARY

A need therefore remains for an improved product of the type mentioned in the introduction, with side flaps folded for packing and attached to the liquid-permeable surface layer in a controlled and secure manner, and for such a product with a maintained or increased capacity for admitting liquid.

According to an embodiment of the present invention, an article of the type referred to in the introduction is characterized in that the side flaps are connected to the liquid-permeable surface layer by a mechanical connection.

In a preferred embodiment, the mechanical connection comprises punctiform or line-shaped indentations brought about by indenting material from the side flaps into the underlying material of the liquid-permeable surface layer so that a permanent deformation of these materials is brought about in the punctiform or line-shaped indentations.

This mechanical connection, what may be referred to as mechanical tacking, can be brought about by, for example, a squeezing roller with a number of projecting squeezing means in the form of cold or hot grooves, spikes or needles. Another way of bringing about mechanical tacking is to use ultrasound technology, where the article is fed through a nip having an ultrasound unit and a counter-tool with a number of different projecting squeezing means. When using ultrasound technology, it is preferred if the articles are relatively thin. Thick articles may require too much energy in order to bring about economic and sufficiently rapid tacking. By tacking the side flaps to the liquid-permeable surface layer of the article, it is possible to position the side flaps throughout the manufacturing process until the article is folded for packing, packed and supplied to the consumer. The tacking points connecting the side flaps to the liquid-permeable surface layer are detachable in such a manner that only a small force is required to free the side flaps from the liquid-permeable surface layer. The strength of the mechanical connection between the tacked-together materials at the tacking points is not to be so great that the materials are torn apart around the tacking points when the tacking points are pulled apart/opened.

According to a preferred embodiment of the invention, the side flaps of the article are folded against the liquid-permeable surface layer in such a manner that the longitudinal outer edges of the side flaps do not overlap one another and that the side flaps are tacked to the liquid-permeable surface layer by a number of tacking points in a central area in the longitudinal direction of the article. The tacking is carried out by, for example, a squeezing roller with a number of projecting squeezing means in the form of spikes or needles.

The squeezing means of the squeezing roller are preferably arranged so as to extend over at least a part of the side flaps and one or more areas between the longitudinal outer edges of the side flaps. By having the squeezing means of the squeezing roller extend over an area between the longitudinal outer edges of the side flaps, the side flaps are tacked even though the folding of the side flaps may vary, that is to say when the distance between the longitudinal outer edges of the side flaps varies between different articles.

With mechanical tacking it is also possible to make holes/depressions in the places at which the squeezing means of the squeezing roller are pressed into the liquid-permeable surface layer and, if appropriate, on into an underlying absorption layer. The holes/depressions in the surface layer of the article have been found to contribute to a larger liquid-receiving surface area and to providing a surface structure where the liquid is allowed to remain a short while in the depressions before it is absorbed into the absorption material.

It has also been found that an article having holes/depressions in the way described above provides more rapid admission of received liquid through the liquid-permeable surface layer on down to underlying material. In order further to improve the transport of liquid from the liquid-permeable surface layer of the article to underlying material, the tacking is carried out by a squeezing roller with squeezing means which are tapering, for example conical, the most pointed part facing towards the article. The conical squeezing means contribute to the holes/depressions down into the article having a conical appearance with a wider dimension of the hole/depression at the surface of the article and a decreasing dimension into the product. Conical holes/depressions positioned in such a manner as described above can provide an increased capillary force in the direction from the wide opening of the hole/depression to the less wide opening of the hole/depression down in the article. The spreading rate of the liquid down into the conical hole thus increases compared with if the dimension of the hole/depression was constant over the entire depth.

When the side flaps are tacked to the surface layer, it can be difficult to keep the side flaps intact, so that these are not perforated in the areas of the tacking, unless the side flaps are made from material having stretchability. Side flaps comprising stretchable material will quite simply accompany the tacking tool down into the article without the material of the side flaps coming apart. If a less stretchable or completely rigid material is used for the side flaps, it is of greater importance where the tacking takes place over the surface of the side flaps compared with if the article had very stretchable side flaps. If the holes in the side flaps lie in an area close to the bending lines of the side flaps in such a manner that these come to lie on the side which is not folded around the edge of the briefs and attached to the underside thereof, there is an obvious risk that the briefs will be soiled by received liquid as there is a risk that the liquid can penetrate down through the holes. The bending lines of the side flaps mean the folding lines on the side flaps which are brought about during folding for packing and, in the packing state, constitute a part of the longitudinal side edges of the article. It is preferred that the distance between the tacking points and the bending lines of the side flaps is greater than 10 mm. If the distance between the tacking points and the bending lines of the side flaps is considerably smaller than 10 mm, the holes which are made by the squeezing means of the squeezing roller may come to lie on that side in the briefs which lies next to the wearer during use when the side flaps have been folded around the edges of the briefs in the crotch area. Any holes on the side flaps which should come to lie on that side in the briefs which lies next to the wearer during use would contribute to an increased risk of leakage because it is possible for the received liquid to penetrate down through the holes to the briefs.

Depending on the extent and positioning of the tacking over the article and the difference in density which arises between a non-tacked area and a tacked area, folding lines are obtained in the article, which can improve the flexibility of the product and its fit against the body of the wearer. For example, these folding lines can be designed so as, in a fitted article, to provide a raised portion, what is known as a hump, intended to come up against the genitals of the wearer so as effectively and directly to catch liquid when it leaves the body of the wearer. According to another embodiment, the side flaps of the article are tacked detachably to the liquid-permeable surface layer by a number of rows of successive longitudinal punctiform or dash-shaped indentations close to the two longitudinal outer edges of the side flaps. The longitudinal tacking points can also be made a little way further in on the side flaps in the direction towards the bending line of the side flaps, but it is preferred in this case that the distance between the tacking points and the bending lines of the side flaps is greater than 10 mm.

According to a further embodiment, the side flaps of the article are tacked detachably to the liquid-permeable surface layer by a number of rows of successive longitudinal punctiform or dash-shaped indentations arranged over the side flaps in the transverse direction. For the same reason as in preceding embodiments, it is preferred that the distance between the tacking points and the bending lines of the side flaps does not fall considerably below 10 mm. The embodiments described above can be combined with one another, that is to say that the side flaps of the article are tacked detachably to the surface layer by a number of rows of successive longitudinal punctiform or dash-shaped indentations arranged over the side flaps in the transverse and longitudinal direction in combination with a number of tacking points in a central area in the longitudinal direction of the article. It is also possible for the tacking points to extend diagonally over the side flaps of the article.

According to a further embodiment of the invention, the side flaps are folded against the liquid-permeable surface layer in such a manner that the longitudinal outer edges of the side flaps overlap one another and that the side flaps are tacked to the liquid-permeable surface layer by tacking points which are common to the side flaps. The tacking points can include a number of points arranged in a central area in the longitudinal direction of the article, be in the form of lines over the side flaps in the longitudinal direction or transverse direction, or combine tacking in different directions and patterns.

According to a further embodiment, the side flaps of the article are tacked detachably to the liquid-permeable surface layer by at least one tack in the form of a continuous longitudinal line arranged over each side flap. This embodiment provides depressions/ducts in the surface layer of the article on down into underlying absorption material, which contributes to a larger liquid-receiving surface area and a surface structure in which the liquid is allowed to remain a short while before the liquid is absorbed into the absorption material. This illustrative embodiment is less exacting in terms of the stretchability of the component materials because the loading of the material is less as the squeezing area is greater when a continuous squeezing pattern is used compared with the embodiments above where small points or dashes are used.

It is not necessary for tacking in the form of lines to have the same width along the entire extent of the lines, but these can of course differ in width over their extent. One reason for selecting tacking in the form of lines with different widths along the extent of the lines may be to obtain a more attractive appearance of the liquid-permeable surface layer of the article. Another reason for selecting different widths along the extent of the lines may be that a larger liquid-receiving surface structure is desired in the liquid-permeable surface layer at certain places on the article, for example at the wetting point of the article where the liquid is allowed to remain a short while before the liquid is absorbed into the absorption material.

It is also possible for tacking in the form of lines to have different depth along the extent of the lines. One reason for tacking in the form of lines having different depth is that, in addition to tacking of the side flaps to the surface layer of the article, ducts into the underlying absorption core with different density along the extent of the lines are also obtained. In the case of increased density, more rapid spreading of the liquid along the squeezed area is obtained. Depending on the extent and positioning of the tacking over the article and the difference in density which arises between a non-tacked area and a tacked area, folding lines are obtained in the article, which can improve the flexibility of the product and its fit against the body of the wearer.

Tacking, without the side flaps or the liquid-permeable surface layer coming apart, can also be effected on articles with side flaps which are provided, in the area of the tacking points, with means of attachment and a protective layer over the means of attachment on that side of the side flaps which is to be attached to the outside of the briefs during use, on condition of course that the protective layer does not come apart either.

BRIEF DESCRIPTION OF DRAWINGS

A preferred embodiment of the invention will be described in greater detail below with reference to the figures shown in the accompanying drawings, in which.

DETAILED DESCRIPTION OF PREFERRED EMBODIMENTS

The embodiments relate to absorbent articles in the form of sanitary towels, but the invention can of course be applied to panty liners, incontinence pads, nappies or the like, where the article comprises side flaps which are folded for packing.

Figure 1:
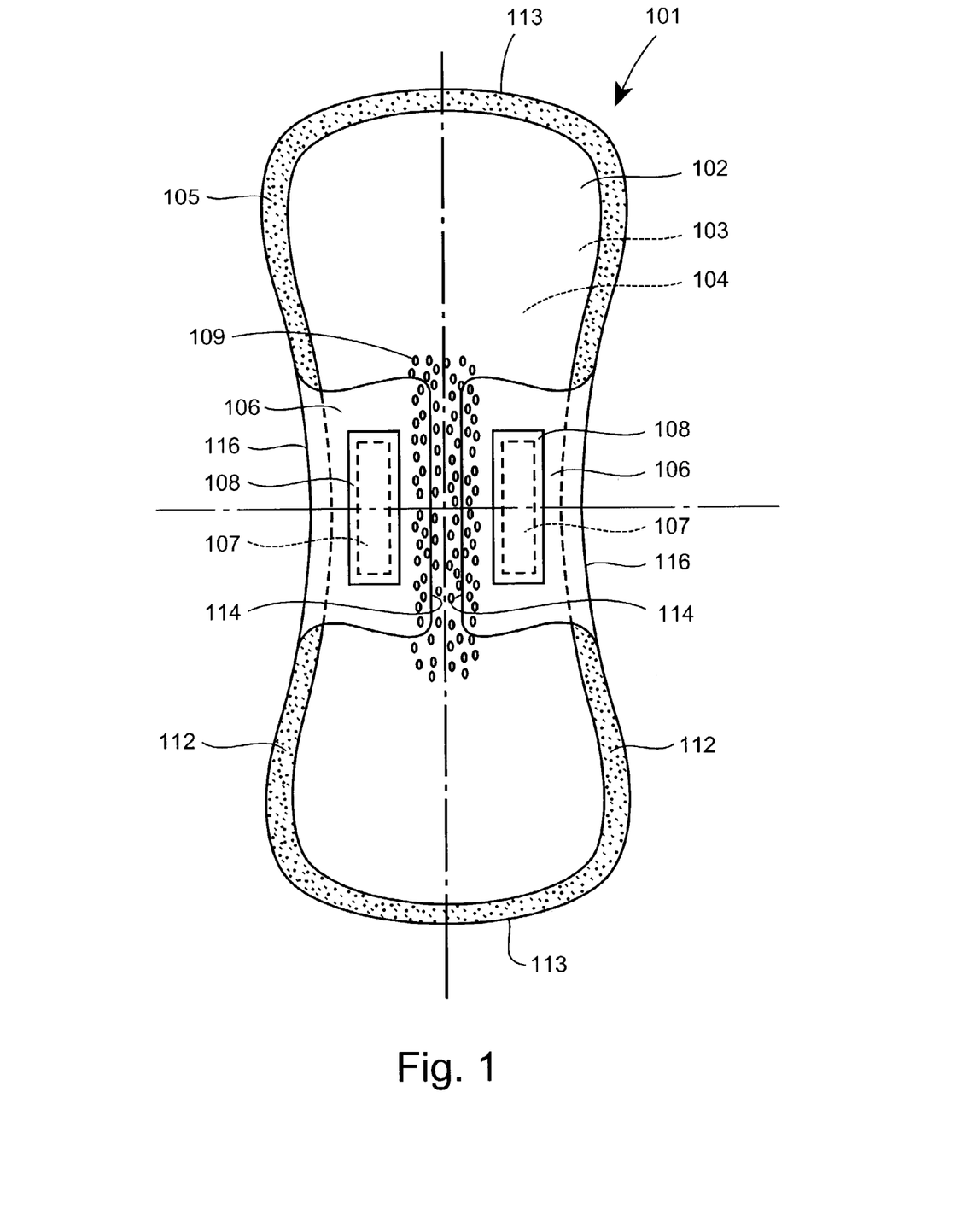
FIG. 1 shows a sanitary towel, seen from the side which is to face the wearer during use, with the side flaps folded and attached in the packing position.
Figure 2:
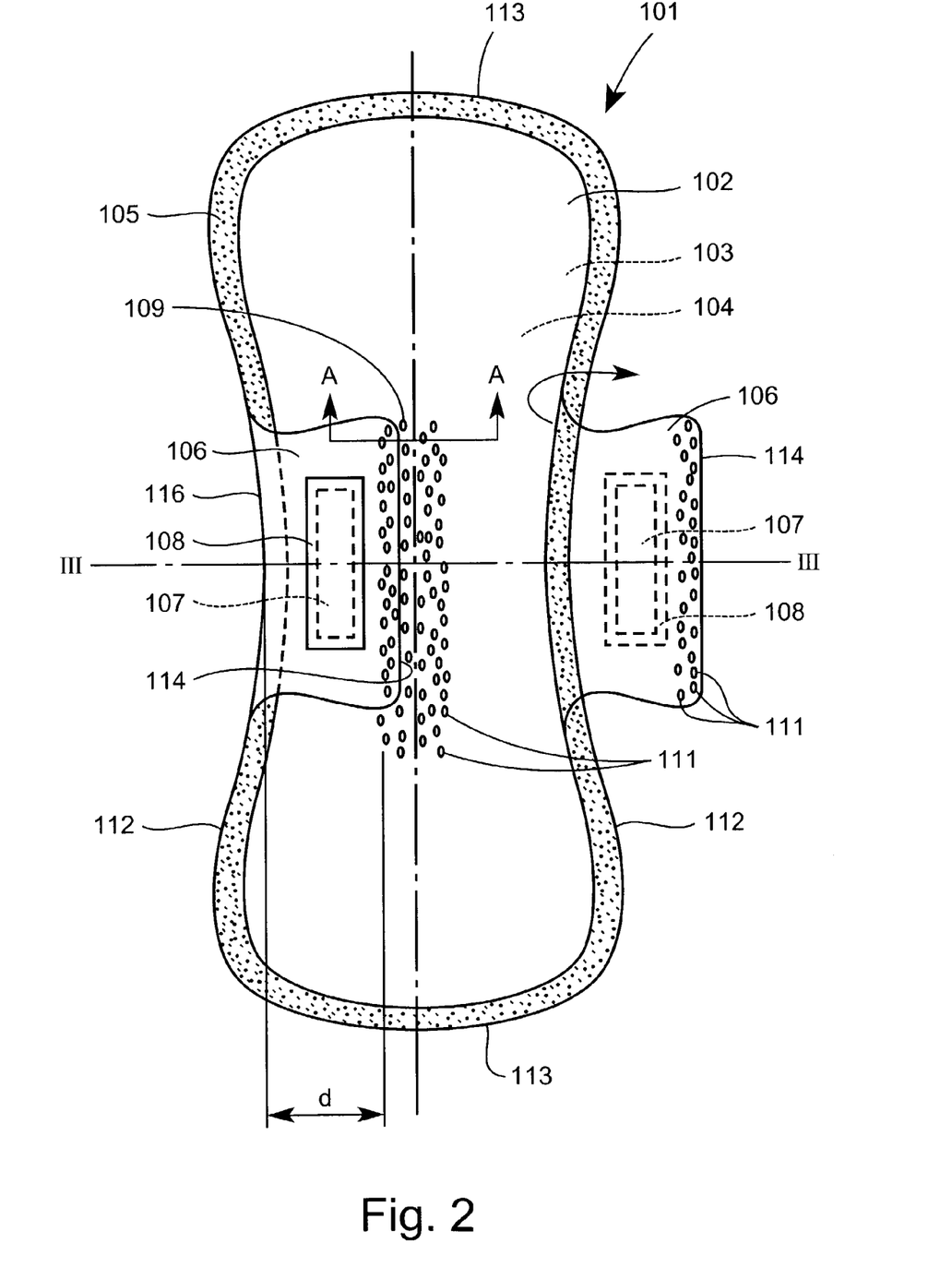
FIG. 2 shows the sanitary towel illustrated in FIG. 1, one side flap of which has been folded up from the liquid-permeable surface layer of the sanitary towel.
Figure 3A:
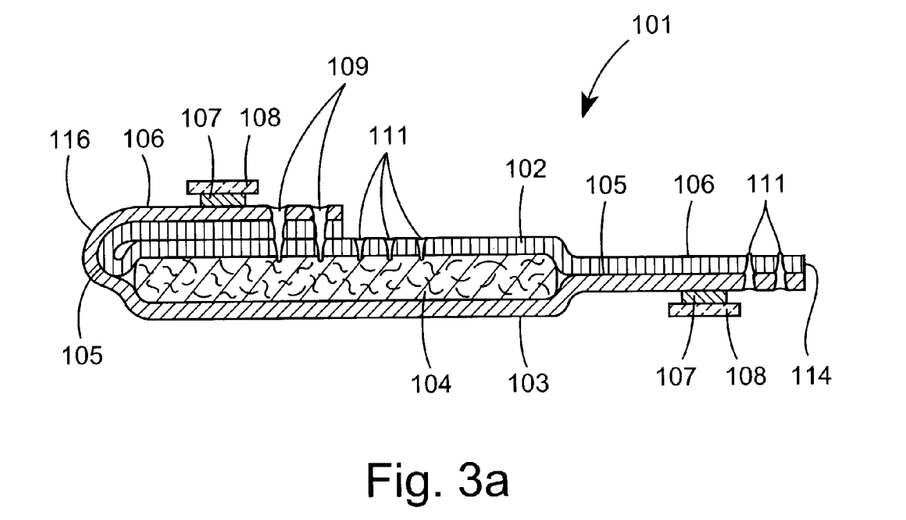
FIG. 3a shows a section along the line III-III through the sanitary towel in FIG. 2.
Figure 3B:
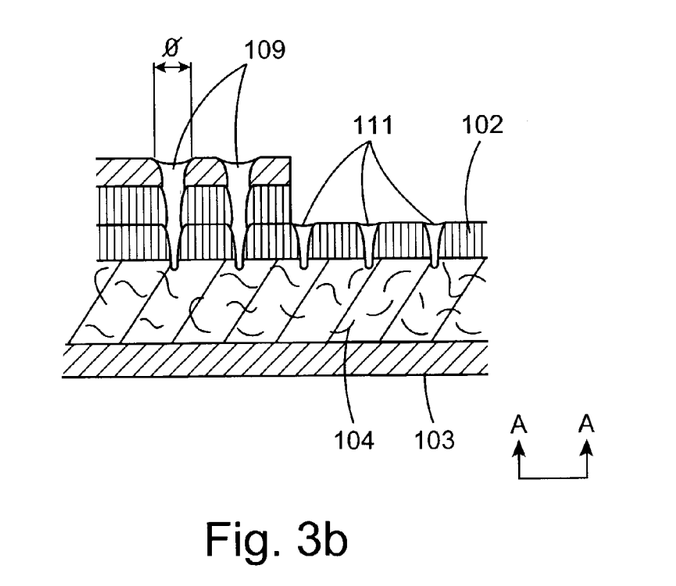
FIG. 3b shows a section along the line A-A through the sanitary towel in FIG. 2.

FIGS. 1, 2, 3a and 3b show a sanitary towel 101 seen from the side which is intended to face the wearer during use, which sanitary towel 101 comprises two transverse end edges 113 and two longitudinal side edges 112. The sanitary towel 101 shown in FIG. 1 comprises side flaps 106 which are located in a packing position, that is to say folded in against and attached to the liquid-permeable surface layer 102. The difference between FIGS. 1 and 2 is that the towel 101 in FIG. 2 illustrates the towel 101 when one side flap 106 is lifted up and away from the liquid-permeable surface layer 102. The side flaps 106 are lifted up from the liquid-permeable surface layer in order, for use, to be folded around the leg openings of the briefs in the crotch area. FIG. 3a shows a section III-III through the sanitary towel in FIG. 2. FIG. 3b shows a section A-A through the sanitary towel in FIG. 2.

A liquid-permeable surface layer 102 is arranged on that side of the sanitary towel 101 which is intended to face the wearer. The liquid-permeable surface layer 102 suitably includes a soft, skin-friendly material. Examples of suitable liquid-permeable materials are types of non-woven fabrics. Another example of liquid-permeable material is a layer of continuously longitudinal fibres. Other liquid-permeable materials which can be used are perforated plastic films, flocked surface material, net, knitted, crocheted or woven textiles and combinations and laminates of the listed material types.

The sanitary towel 101 also comprises a liquidtight backing layer 103 arranged on that side of the sanitary towel which is to face away from the wearer. In the illustrative embodiment shown, a thin flexible plastic film is used as the liquidtight backing layer 103. Examples of suitable films are polypropylene and polyethylene films or laminates of these. The backing layer 103 is advantageously produced in such a manner that it is liquidtight but vapour-permeable. Other materials suitable for the liquidtight backing layer 103 can include, for example, liquidtight but vapour-permeable filled plastic films, foamed materials with filled cells, textile materials, for example non-wovens, or laminates having several textile layers or layers of film and textile material. Examples of liquidtight but air-permeable textile materials are laminates having one or a number of layers of spunbond non-woven joined together with meltblown non-woven layers, filled plastic film, waxed material layers and treated wadding.

Positioned between the liquid-permeable surface layer 102 and the liquidtight backing layer 103 is an absorbent core 104 which can comprise one or more material layers. Suitable material for the absorbent core 104 may be, for example, cellulose pulp. This may be in rolls, bales or sheets which are dry-defibred and converted in fluffed form into a pulp mat, if so desired with the addition of what are known as superabsorbents, which are polymers with the capacity to absorb several times their weight of water or bodily fluid. Examples of other materials which can be used are various types of regenerated cellulose, for example viscose fibres as described in SE 9903070-2. Natural fibres such as cotton fibres, peat or the like can also be used. It is of course also possible to use absorbent and/or hydrophilic synthetic fibres or mixtures of natural fibres and synthetic fibres. Cellulose-based foam or synthetic foam can of course be used for the purpose.

In instances when the absorbent core is constructed from a number of layers, it is very common for the absorbent core 104 to comprise a layer, positioned next to the liquid-permeable surface layer 102, which is designed in such a manner that it can rapidly transport liquid away from the liquid-permeable surface layer 102. Within the sector, this material positioned next to the liquid-permeable surface layer 102 is in most cases referred to as an acquisition layer. The acquisition layer can comprise, for example, an open wadding structure made up of natural fibres and/or synthetic fibres, or an airlaid material comprising cellulose fibres and/or synthetic fibres. Another example of an acquisition material is a foamed material with large open cells for onward transport of liquid to underlying material. The absorbent core 104 can also comprise a spreading layer positioned under the acquisition layer and a storage layer advantageously positioned at the very bottom of the product against the liquidtight backing layer 103. The spreading layer can include, for example, a tissue material, cellulose layer, non-woven layer or the like, which has been treated mechanically or chemically, or the component fibres of which have been controlled during manufacture of the material so as to obtain a specific orientation of component fibres. An example of mechanical treatment of the material in order to obtain spreading in the layer is to change the density of the material, by means of mechanical squeezing, in the form of ducts. An example of chemical treatment is treating the material with a wetting agent applied in the form of lines in the transverse direction and/or longitudinal direction of the material. By manufacturing a material with a specific desired fibre direction, the material is given a natural liquid-spreading capillary structure in the fibre direction.

The two layers, the liquid-permeable surface layer 102 and the liquidtight backing layer 103, are interconnected and form a projecting connecting edge 105 around the longitudinal side edges 112 and transverse end edges 113 of the sanitary towel. The connection can be made using any technique known for the purpose, such as gluing, heat welding, ultrasonic welding or stitching.

The sanitary towel also has two side flaps 106, arranged one on each side of the absorbent core 104, the side flaps 106, in their unfolded or folded-out configuration, projecting in the transverse direction from each longitudinal side edge 112. The shape and size of the side flaps 106 are such that, during use, they can be folded around the leg openings of the briefs. In this embodiment, the side flaps 106 include the liquidtight backing layer 103 and the liquid-permeable surface layer 102 which extend outside the absorbent core 104. The side flaps 106 can of course include separate shaped material pieces which are attached to the longitudinal side edges 112 of the sanitary towel or of only one of the surface layers.

The projecting side flaps 106 have been provided with means of attachment 107 on the surface facing away from the wearer in order that the side flaps 106 lie properly against the outside of the briefs during use. The means of attachment 107 suitably include an adhesive, for example a pressure sensitive hot melt adhesive, which is protected by a removable protective layer 108. The protective layers 108 are intended to protect the adhesive means of attachment 107 from dirt and dust and to prevent the adhesive adhering to other surfaces or to itself until the sanitary towel is to be used. As an alternative to the adhesive means of attachment 107, use can be made of a means of attachment which adheres mechanically, for example touch-and-close material or "stemweb". When a touch-and-close material is used as the means of attachment, the protective layer 108 can be omitted. A means of attachment and a removable protective layer can also be arranged on the surface facing away from the wearer of the essentially liquidtight backing layer 103 in the area of the absorbent core 104 (not shown in figure).

The side flaps 106 of the sanitary towel are folded up against the liquid-permeable surface layer 102 of the sanitary towel and tacked by tacking points 109. Mechanical tacking has been carried out on the sanitary towel in and around the area of the extent of the side flaps in the longitudinal direction and also in the area between the side flaps 106. In this embodiment, the tacking points 109 are positioned in areas which are free of means of attachment 107 and protective layers 108. Positioning the tacking points 109 in areas outside the means of attachment 107 and the protective layers 108 is preferred from the point of view that it is not necessary to take account of or be limited by the materials selected for the means of attachment 107 and the protective layers 108.

When the side flaps 106 are removed from the liquid-permeable surface layer 102, holes and/or depressions 111 down into the liquid-permeable surface layer 102 remain. Depending on the amount of mechanical pressure applied during production of the tacking points 109, and on the component materials of the sanitary towel, depressions/holes 111 of different depths can be obtained. If, for example, a stretchable material is used for the liquid-permeable surface layer 102, this will accompany the tacking tool down into the tacking points 109. If, on the other hand, a rigid material is used for the liquid-permeable surface layer 102, holes will be formed in the liquid-permeable surface layer 102 without the material being drawn down appreciably into the tacking points 109. In the preferred embodiment shown, the holes 111 extend through the liquid-permeable surface layer 102 and on down into the underlying absorbent core 104.

When fibrous materials are tacked, fibre ends of the indented fibrous material will become entangled with fibres in the underlying fibrous material, and an easily detachable connection is obtained. If the indenting is carried out so that the materials are broken, the hole edges will catch on underlying material. Against this background, the tacking should be effected so that holes are formed if the liquid-permeable surface layer includes a non-fibrous material. As mentioned above, the holes formed in the surface layer bring about more rapid penetration of liquid to the underlying core, for which reason it is advantageous from this point of view as well to carry out the tacking so that holes are formed irrespective of whether the liquid-permeable surface layer includes a fibrous material or not. When hot needles are used, it is preferred that the heat is not sufficient to melt the backing layer or any melt fibres included in the liquid-permeable surface layer or in the core. However, a small degree of fusing, especially of the liquidtight surface layer, can be permitted without any risk of the connection between the folded-in side flap and the liquid-permeable surface layer becoming too strong or this surface layer being damaged when this connection is opened.

The tacking points 109 are preferably to be positioned over the side flap 106 at a distance d from the bending line 116 of the side flap in order that the holes 111 formed through the side flaps 106 during mechanical tacking will end up on the outside of the briefs when the side flaps 106 are folded around the leg openings of the briefs in the crotch area. If the distance d is too small, there is a risk that the holes 111 of the side flaps 106 will lie on that side of the briefs which will be exposed to liquid from the wearer, in which case liquid may penetrate through the holes 111 and give rise to leakage onto the underwear of the wearer.

FIG. 3b shows an enlargement of the tacking points 109 and the holes/depressions 111 of the sanitary towel in order to illustrate what was said in the previous paragraph.

Conical needle-shaped tacking tools have been used for the sanitary towel 101 in order to produce conical holes/depressions 111 with the tapering part directed downwards into the sanitary towel so as to bring about a capillary force for the received liquid down into the holes/depressions. The diameter the holes/depressions 111 have right on the surface of the liquid-permeable surface layer 102 is 0.5-5 mm, preferably 1-3 mm, the diameter then decreasing with increasing depth.

Figure 4:
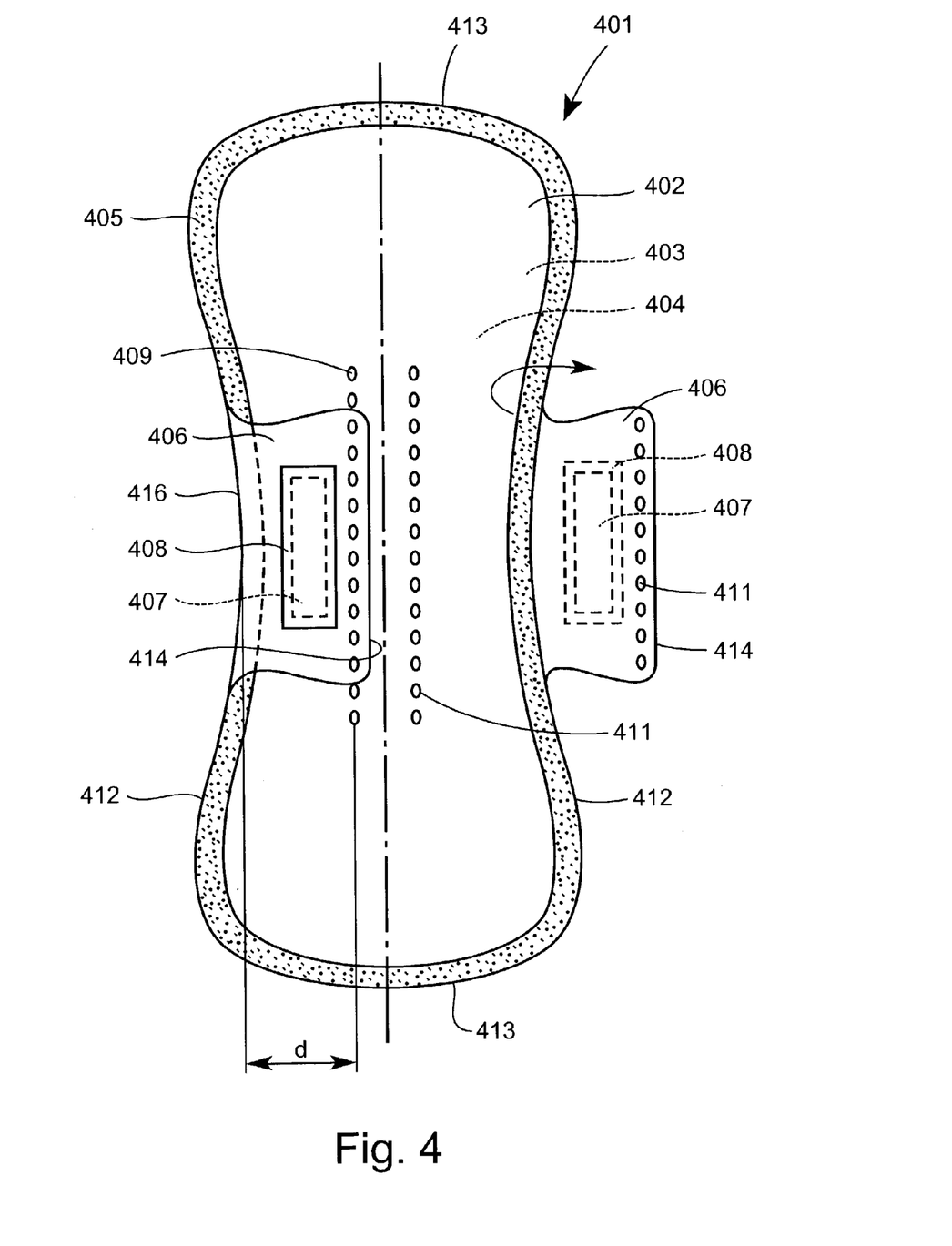
FIG. 4 shows a sanitary towel according to another embodiment of the invention, seen from the side which is to face the wearer during use, one side flap of which is folded up.

FIG. 4 shows a sanitary towel 401 of essentially the same construction as the sanitary towel in FIGS. 1-3b. The numbering of the various parts of the sanitary towel in FIG. 4 is therefore by analogy with that used in the description of the sanitary towel in FIGS. 1-3b. However, the sanitary towel 401 shown in FIG. 4 differs from the sanitary towel 101 described previously in at least one respect, namely in that the tacking is carried out in a different pattern from that shown in FIGS. 1-3. The side flaps 406 of the sanitary towel are folded up against the liquid-permeable surface layer 402 of the sanitary towel and tacked by tacking points 409 positioned one after another in a row directly inside the longitudinal outer edges 414 of the side flaps.

The tacking points 409 are preferably to be positioned over the side flap 406 at a distance d from the bending line 416 of the side flap in order that the holes 411 formed through the side flaps 406 during mechanical tacking will end up on the outside of the briefs when the side flaps 406 are folded around the leg openings of the briefs in the crotch area. If the distance d is too small, the holes 411 of the side flaps 406 will lie on that side of the briefs which will be exposed to liquid from the wearer, and the liquid can then penetrate through the holes 411 and give rise to leakage onto the underwear of the wearer. The material selection for the sanitary towel 401 does not differ from that described for the preceding embodiment described in FIGS. 1-3b.

Figure 5:
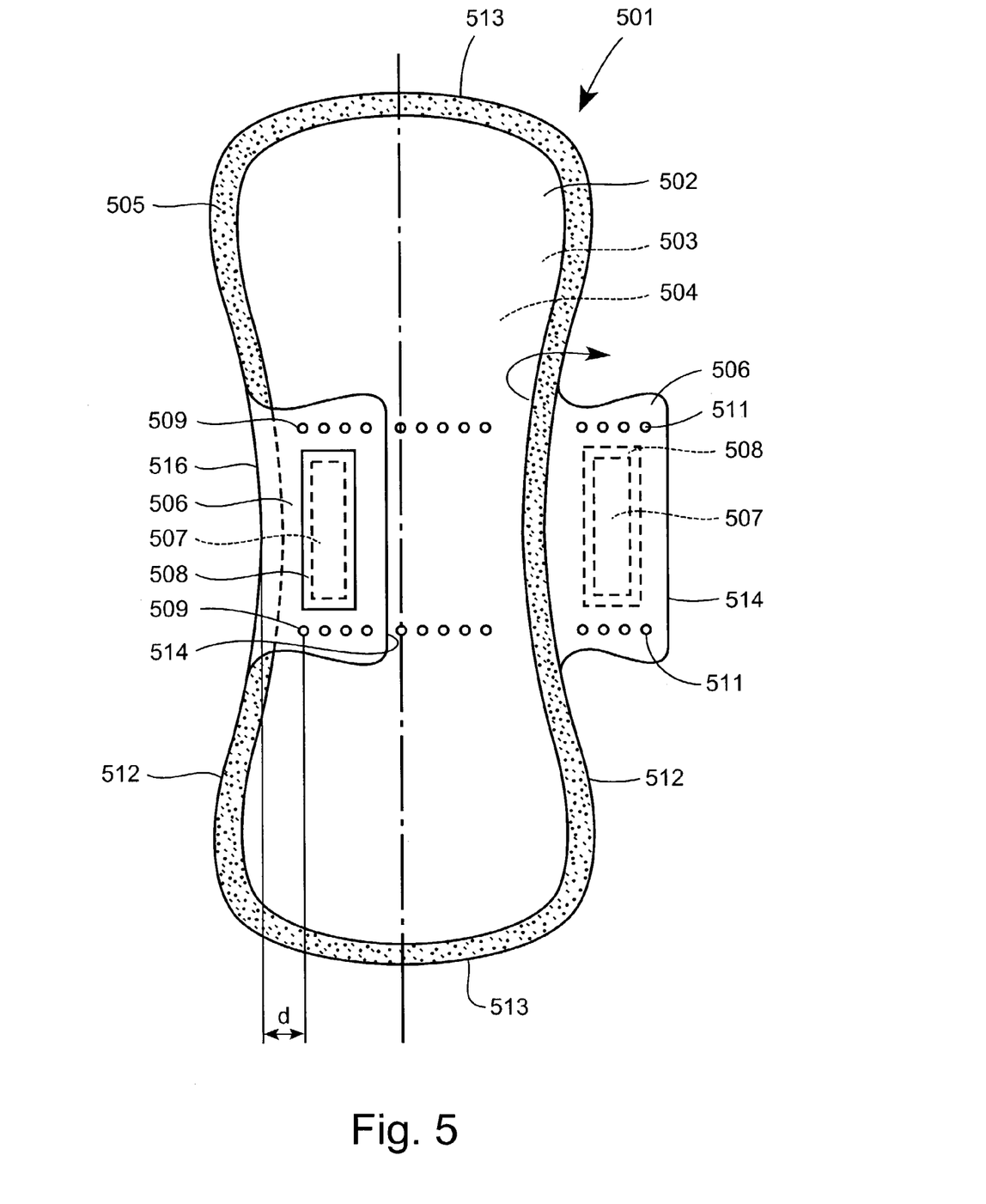
FIG. 5 shows a sanitary towel according to a further embodiment of the invention, seen from the side which is to face the wearer during use.

FIG. 5 shows a sanitary towel 501 of essentially the same construction as the sanitary towel in FIGS. 1-4. The numbering of the various parts of the sanitary towel in FIG. 4 is therefore by analogy with that used in the description of the sanitary towel in FIGS. 1-4. However, the sanitary towel 501 shown in FIG. 5 differs from the sanitary towels 101 and 401 described previously in at least one respect, namely in that the tacking is carried out in a different pattern from that shown in FIGS. 1-3 and 4.

The side flaps 506 of the sanitary towel are folded up against the liquid-permeable surface layer 502 of the sanitary towel and tacked by tacking points 509 positioned one after another in a row directly inside the two transverse outer edges 415 of the side flaps 506. In this embodiment as well, the tacking points 509 are positioned at a distance d from the bending line 516 of the side flap such that the holes 511 formed on the side flaps 506 during mechanical tacking of the side flaps 506 to the liquid-permeable surface layer 502 of the sanitary towel do not end up on the side which will be exposed to the wearer so that received liquid can penetrate through the holes 511 and give rise to leakage onto the underwear of the wearer. The material selection for the sanitary towel 501 does not differ from that described in preceding embodiments.

Figure 6:
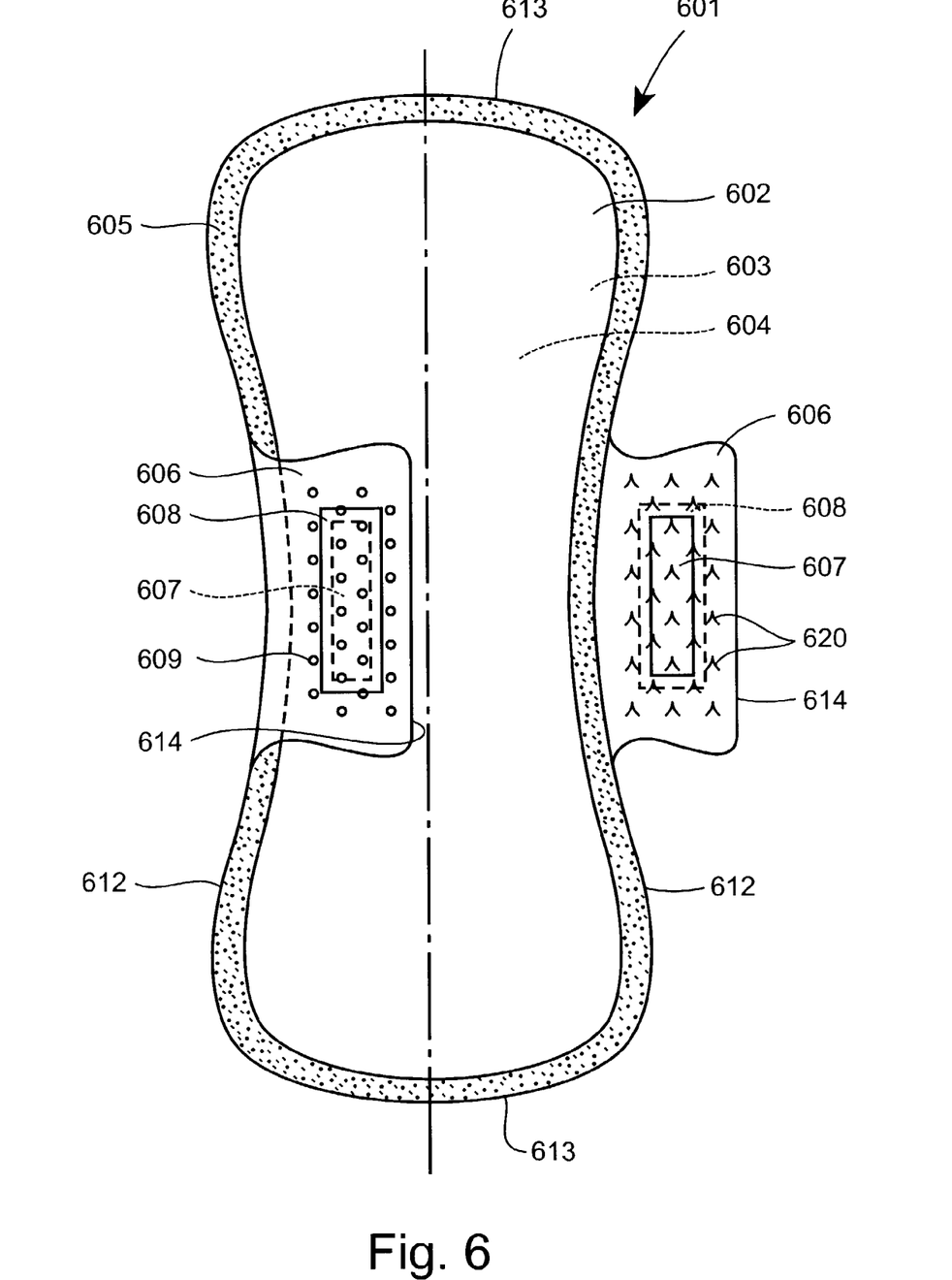
FIG. 6 shows a sanitary towel according to yet another embodiment of the invention, seen from the side which is to face the wearer during use.

FIG. 6 shows a sanitary towel 601 of essentially the same construction as the sanitary towel in FIGS. 1-5. The numbering of the various parts of the sanitary towel in FIG. 4 is therefore by analogy with that used in the description of the sanitary towel in FIGS. 1-5. However, the sanitary towel 601 shown in FIG. 6 differs from the sanitary towels 101, 401 and 501 described previously in at least one respect, namely in that the tacking is carried out in a different pattern from that shown in FIGS. 1-5.

FIG. 6 shows an example of a sanitary towel 601 where side flaps 606 are folded up against the liquid-permeable surface layer 602 of the sanitary towel and where tacking points 609 have also been positioned over the side flaps 606 in the area of means of attachment 607, protective layers 608 and between the side flaps 606. With this embodiment, it is preferable to select stretchable materials for the means of attachment 607, for example PSHM (pressure sensitive hot melt), the protective layer 608, for example siliconized polyethylene film, and the side flaps 606, for example polyethylene film, so that these accompany the tacking tool without any holes being formed, which make it possible for the means of attachment 607 to be exposed, but only depressions 620. If a means of attachment 607 is used which is not an adhesive and does not have to be protected by a protective layer 608, it is permissible for holes to be formed during the tacking operation.

Figure 7:
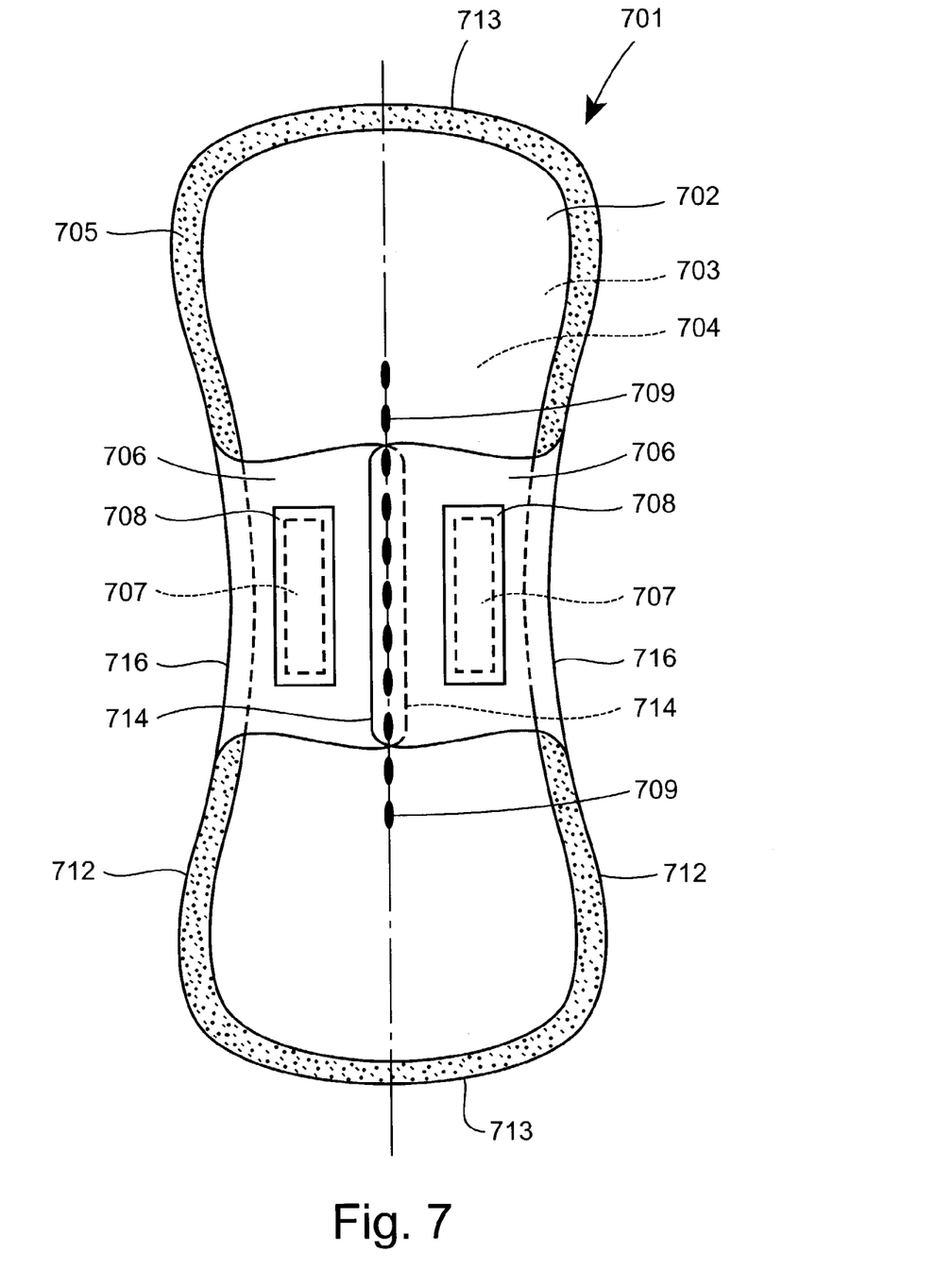
FIG. 7 shows a sanitary towel according to yet another embodiment of the invention, seen from the side which is to face the wearer during use.

FIG. 7 shows a further variant of the invention where the sanitary towel 701 is of essentially the same construction as the sanitary towel in FIGS. 1-6 but where the side flaps 706 are designed in such a manner that, when they are folded up against the liquid-permeable surface layer 702, the side flaps 706 overlap and are tacked by a common longitudinal row of tacking points 709 positioned directly inside the longitudinal outer edges 714 of the side flaps.

Figure 8:
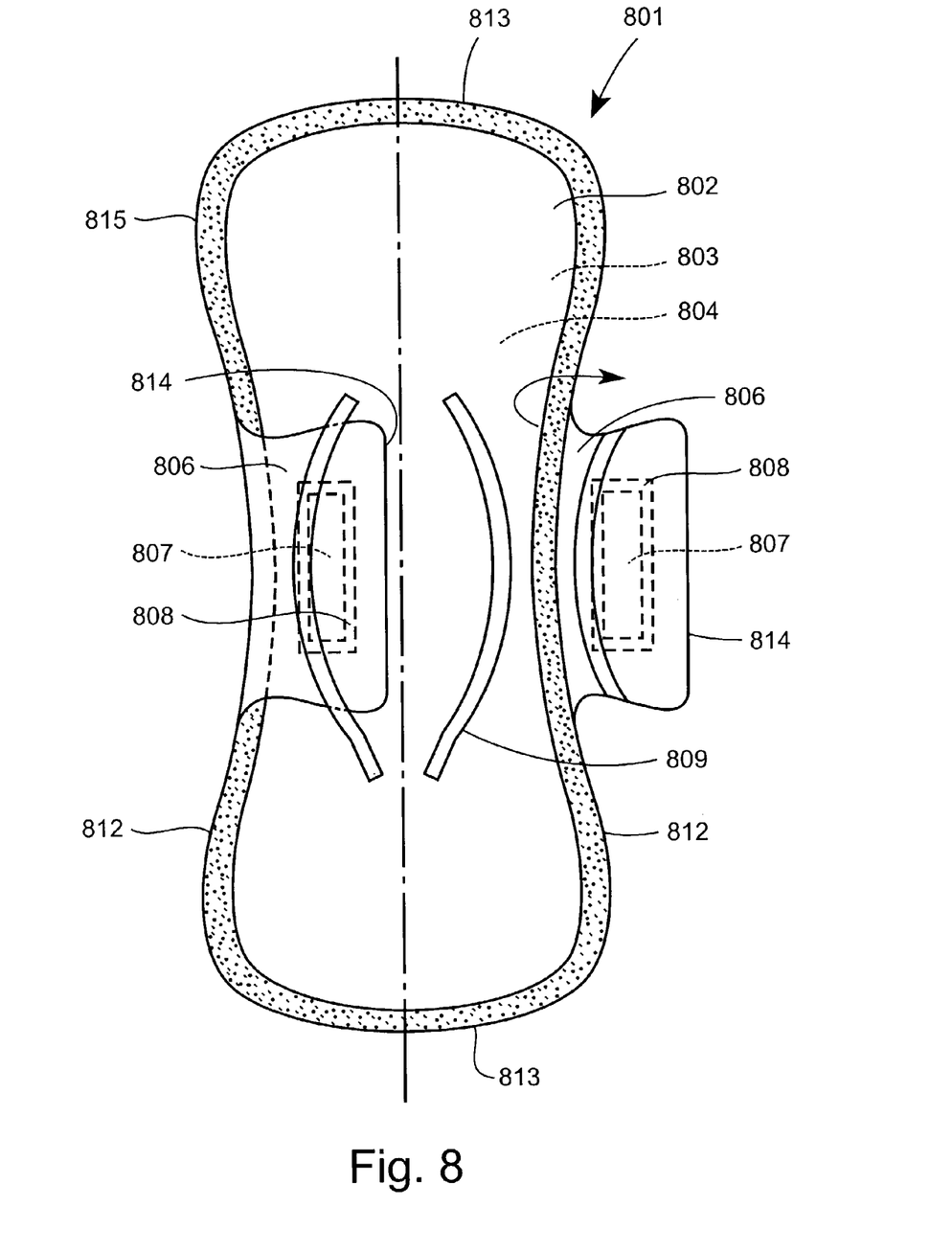
FIG. 8 shows a sanitary towel according to yet another embodiment of the invention, seen from the side which is to face the wearer during use.
Figure 9A:
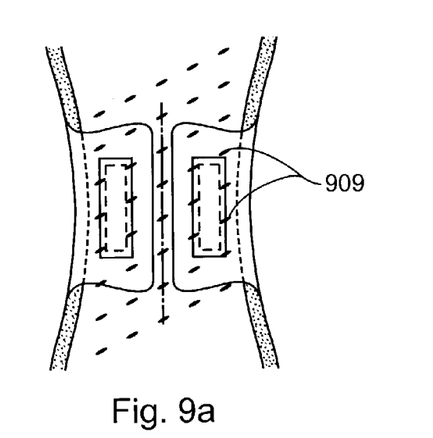
FIGS. 9a-j show further proposals for patterns and positionings of the tacking points other than those already illustrated in preceding figures.
Figure 9B:
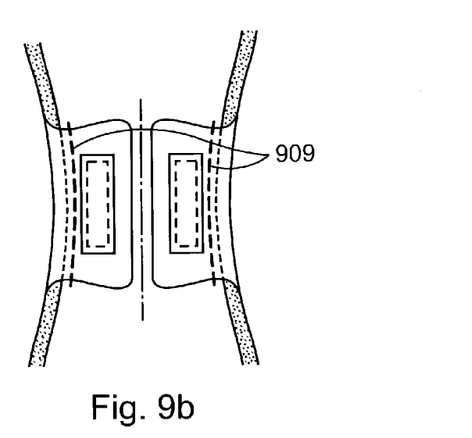
Figure 9C:
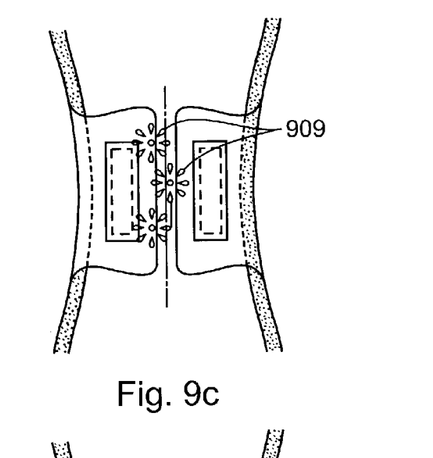
Figure 9D:
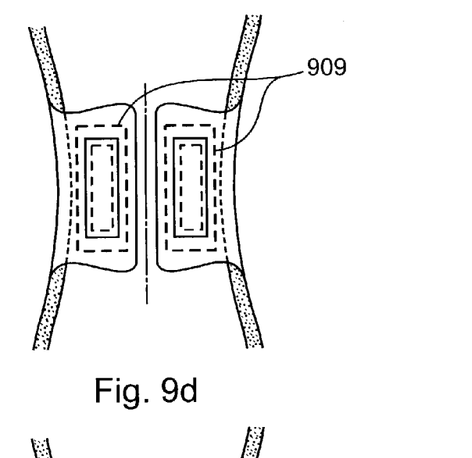
Figure 9E:
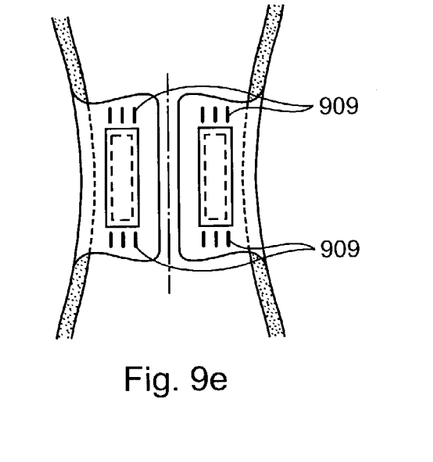
Figure 9F:
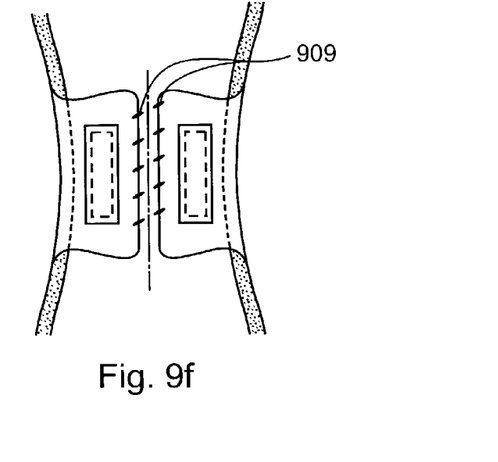
Figure 9G:
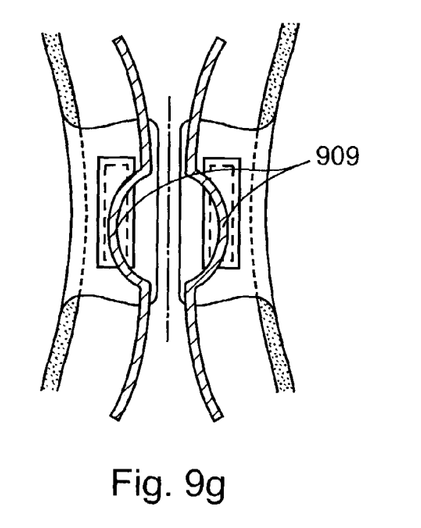
Figure 9H:
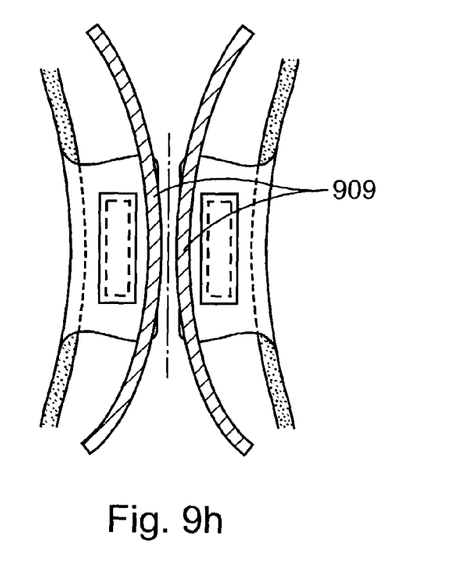
Figure 9I:
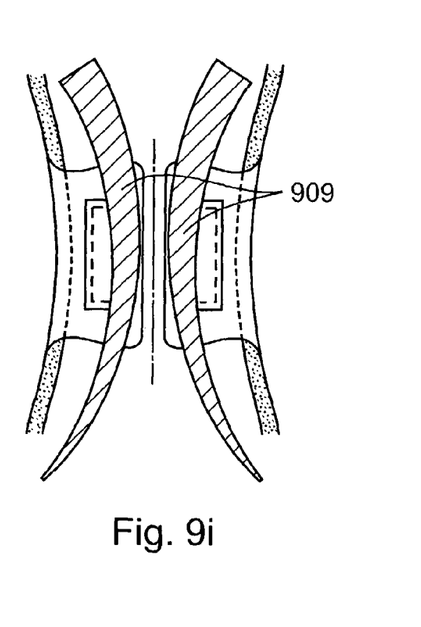
Figure 9J:
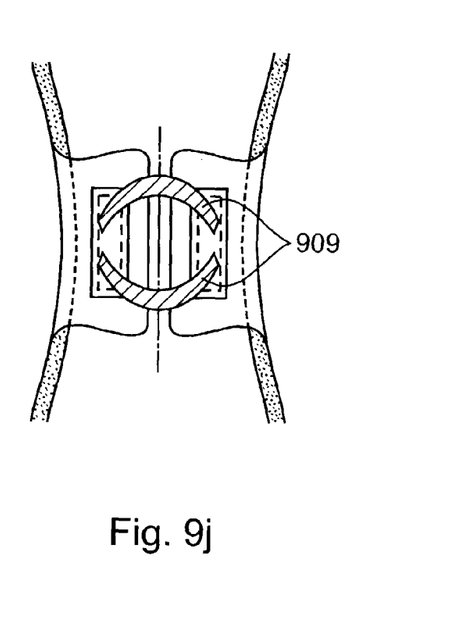

FIG. 8 shows a further variant of the invention where the sanitary towel 801 is of essentially the same construction as the sanitary towel in FIGS. 1-7 but where the side flaps 806 are tacked down against the liquid-permeable surface layer 802 by at least one longitudinal tack 809 in the form of a continuous line for each side flap 806. The width of the tack 809 is around 1-10 mm, preferably 2-6 mm. FIG. 8 shows an example of how tacking lines 809 can be shaped over the sanitary towel. The tacking lines 809 in FIG. 8 are shaped like curves which are positioned over the side flaps 806 and curve towards the longitudinal edges 812 of the sanitary towel.

It is not critical for the sanitary towel described in the embodiment 801 where the tacking 809 is positioned in relation to the bending lines 816 of the side flaps because the mechanical tacking 809 in the form of a continuous line gives a contact area which is considerably greater and a linear pressure between the squeezing means and the material which is lower compared with if the tacking were to include points as described previously in all the embodiments above. By using tacking 809 in the form of a line, it is easier to avoid holes through the material of the side flaps 806 occurring. The pressure applied to the tacking means should of course always be balanced against the material depending on the material selected for use.

The sanitary towel described in FIG. 8 has been provided with tacking 809 in the form of lines of the same width along the entire extent of the lines, but it is of course possible to use tacking in the form of lines which are not of uniform width over their extent. It is also possible for tacking in the form of lines to be positioned across the sanitary towel.

FIGS. 9a-9j show further variants of how tacking points or tacking lines 909 can be positioned over the side flaps 906 and the sanitary towel 901 in order to hold the side flaps 906 down against the liquid-permeable surface layer 902 of the sanitary towel 901 and partly to form decorative patterns.

The indenting of tacking points, tacking dashes or tacking lines can also be effected by means of an ultrasound unit and a counterstay roller provided with a counterstay pattern corresponding to the desired tacking pattern. When use is made of ultrasound technology, however, it is preferred that the energy supplied is not so great that melting of a material or the materials is caused, or use made of non-meltable materials. In this case as well, however, some fusing of the materials can be permitted; in particular, the liquidtight surface layer can be allowed to melt somewhat without risk of the connection of the side flap to the liquid-permeable surface layer becoming too strong. It is also possible to use melting in order to produce easily detachable connections, for example by mixing a small number of melt fibres into fibrous materials. By selecting meltable materials with different melting points, the melting can also be controlled.

The invention is not to be regarded as being limited by the illustrative embodiments described here. Furthermore, all possible combinations and variants of the illustrative embodiments described are intended to fall within the scope of the invention.

What is claimed is:

1. An absorbent article comprising:
   a) a main body comprising:
      two transverse end edges;
      two longitudinal side edges;
      a liquid-permeable surface layer;
      an essentially liquid-tight backing layer; and
      an absorbent core located between the liquid-permeable surface layer and the essentially liquid-tight backing layer; and
   b) a plurality of side flaps, one side flap extending outside beyond the longitudinal side edges of the main body,
   wherein, each side flap is folded along a bending line and folded against the main body,
   wherein, the folded side flaps are detachably connected to the liquid-permeable surface layer of the main body in an area of the main body,
   wherein the side flaps are connected to the liquid-permeable surface of the main body layer by a mechanical connection that comprises a plurality of punctiform, dash-shaped, or line-shaped indentations brought about by indenting material from the side flaps into an underlying material of the liquid-permeable surface layer of the main body so that a permanent deformation of these materials is brought about in the punctiform, dash-shaped, or line-shaped indentations, and
   wherein a plurality of openings extend through the side flaps into the underlying material of the liquid-permeable surface layer of the main body; wherein when the side flaps are folded against the main body, within an area of the punctiform, dash-shaped, or line-shaped indentations, a material of the side flaps and the liquid-permeable surface layer of the main body being permanently deformed in an area along a periphery of each opening.

2. The absorbent article according to claim 1, wherein the mechanical connection for each side flap comprises one or more rows of punctiform, dash-shaped or line-shaped indentations.

3. The absorbent article according to claim 2, wherein the mechanical connection extends over an entire length of the side flaps in a longitudinal direction of the article.

4. The absorbent article according to claim 2, wherein the mechanical connection includes at least one transverse row of punctiform indentations which extends over a part of both side flaps.

5. The absorbent article according to claim 1, wherein the mechanical connection is located at a distance from the bending line of the side flap greater than 10 mm.

6. The absorbent article according to claim 1, wherein the openings extend through the liquid-permeable surface layer and into the absorbent core.

7. The absorbent article according to claim 6, wherein the openings taper in a direction towards the absorbent core.

8. The absorbent article according to claim 1, wherein a diameter of the openings on a surface of the liquid-permeable surface layer is 0.5-5 mm.

9. The absorbent article according to claim 8, wherein the diameter is 1-3 mm.

10. The absorbent article according to claim 1, wherein the mechanical connection includes a number of line-shaped indentations where a width of the line-shaped indentations is 1-10 mm.

11. The absorbent article according to claim 10, wherein the width of the line-shaped indentations is 2-6 mm.

12. The absorbent article according to claim 10, wherein the width of the line-shaped indentations varies along a length of the indentations.

13. The absorbent article according to claim 10, wherein a depth of the line-shaped indentations varies along a length of the indentations.

14. The absorbent article according to claim 10, wherein the line-shaped indentations extend into the absorbent core.

15. The absorbent article according to claim 1, wherein the side flaps have a means of attachment on a side which is to face an outside of a wearer's briefs during use, and wherein the mechanical connection is located outside an area of the means of attachment of the side flaps.

16. The absorbent article according to claim 15, wherein the mechanical connection includes a number of line-shaped indentations where a width of the line-shaped indentations is 1-10 mm.

17. The absorbent article according to claim 16, wherein the width of the line-shaped indentation is 2-6 mm.

18. The absorbent article according to claim 16, wherein the width of the line-shaped indentations varies along a length of the indentations.

19. The absorbent article according to claim 16, wherein a depth of the line-shaped indentations varies along a length of the indentations.

20. The absorbent article according to claim 16, wherein the line-shaped indentations extend into the absorbent core.

21. The absorbent article according to claim 1, wherein the mechanical connection extends over the absorbent core.

22. The absorbent article according to claim 21, wherein the mechanical connection includes a number of line-shaped indentations where a width of the line-shaped indentations is 1-10 mm.

23. The absorbent article according to claim 22, wherein the width of the line-shaped indentation is 2-6 mm.

24. The absorbent article according to claim 22, wherein the width of the line-shaped indentations varies along a length of the indentations.

25. The absorbent article according to claim 22, wherein a depth of the line-shaped indentations varies along a length of the indentations.

26. The absorbent article according to claim 22, wherein the line-shaped indentations extend into the absorbent core.

27. The absorbent article according to claim 1, wherein the absorbent article is a sanitary towel, a panty liner, or an incontinence pad.

28. The absorbent article according to claim 1, wherein the absorbent core is located in the main body of the absorbent article and one or more of the plurality of side flaps.

29. An absorbent article comprising:
 a) a main body comprising:
  two transverse end edges;
  two longitudinal side edges;
  a liquid-permeable surface layer;
  an essentially liquid-tight backing layer; and
  an absorbent core located between the liquid-permeable surface layer and the essentially liquid-tight backing layer; and
 b) a plurality of side flaps, one side flap extending outside beyond the longitudinal side edges of the main body,
 wherein, each side flap is folded along a bending line and folded against the main body,
 wherein, the folded side flaps are detachably connected to the liquid-permeable surface layer of the main body in an area of the main body,
 wherein the side flaps are connected to the liquid-permeable surface of the main body layer by a mechanical connection that comprises a plurality of punctiform, dash-shaped, or line-shaped indentations brought about by indenting material from the side flaps into an underlying material of the liquid-permeable surface layer of the main body so that a permanent deformation of these materials is brought about in the punctiform, dash-shaped, or line-shaped indentations, and
 wherein a plurality of openings extend through the side flaps into the underlying material of the liquid-permeable surface layer of the main body; wherein when the side flaps are folded against the main body, within an area of the punctiform, dash-shaped, or line-shaped indentations, a material of the side flaps and the liquid-permeable surface layer of the main body being permanently deformed in an area along a periphery of each opening,
 wherein the bending line is at a first edge of each of the side flaps; and
 wherein the mechanical connection for one side flap is located at a portion of that side flap that is spaced from the bending line of that side flap.

30. The absorbent article according to claim 1, wherein the bending line is at the longitudinal side edge of the main body and the mechanical connection for one side flap is located at a portion of that side flap that is distally spaced from the bending line of that side flap.

* * * * *